United States Patent [19]

Liang et al.

[11] Patent Number: 5,059,202
[45] Date of Patent: Oct. 22, 1991

[54] TENDON APPROXIMATOR

[75] Inventors: Marc D. Liang; Krishna Narayanan, both of Pittsburgh; Eugene D. Ross, Southampton, all of Pa.

[73] Assignee: The Montefiore Hospital Association of Western Pennsylvania, Pittsburgh, Pa.

[21] Appl. No.: 541,505

[22] Filed: Jun. 21, 1990

Related U.S. Application Data

[62] Division of Ser. No. 263,518, Oct. 27, 1989, Pat. No. 4,957,500.

[51] Int. Cl.$^5$ .............................................. A61B 17/00
[52] U.S. Cl. .................................... 606/150; 606/157
[58] Field of Search ................ 606/150, 157, 158, 221

[56] References Cited

U.S. PATENT DOCUMENTS

| | | | |
|---|---|---|---|
| 4,316,470 | 2/1982 | Braun et al. | 606/150 |
| 4,630,608 | 12/1986 | Arroyo | 606/150 |
| 4,635,636 | 1/1987 | Goldstein | 606/150 |
| 4,723,548 | 2/1988 | Lalonde | 606/150 |

*Primary Examiner*—Stephen C. Pellegrino
*Assistant Examiner*—Gary Jackson
*Attorney, Agent, or Firm*—Harry B. Keck

[57] ABSTRACT

A tendon approximator employs two connected, normally closed clamps, which are each formed from two extruded elements. The two extruded elements are connected together in their mid-region by means of non-circular cam on a base element and a corresponding non-circular cam surface on a clamping element. In the normally closed position of the individual clamps, the cam and cam surface urge the device into a jaw-closed position with the handles being spaced apart. In a preferred embodiment two of the clamps are connected by means of rods extending through corresponding handle portions of the two clamps.

3 Claims, 3 Drawing Sheets

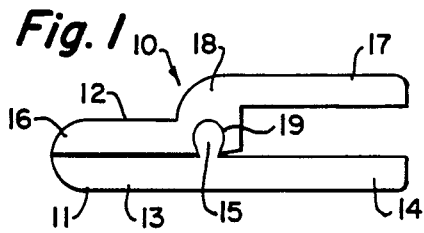
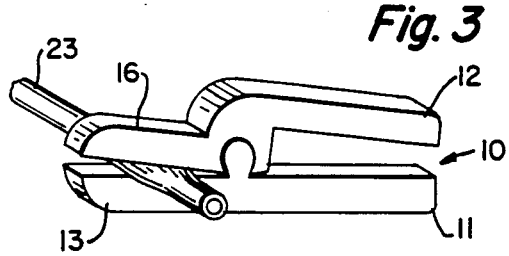
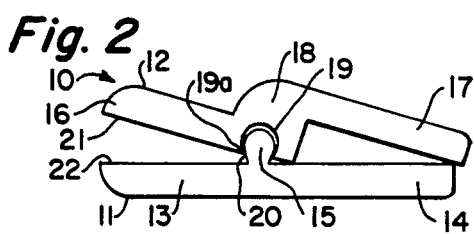
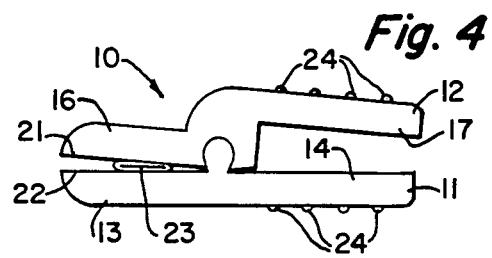
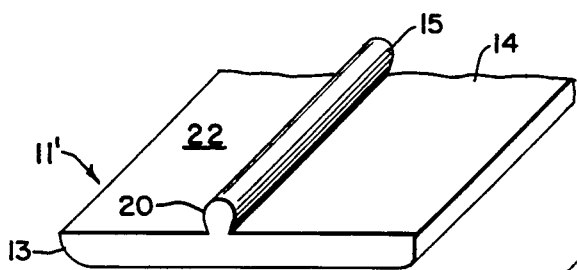
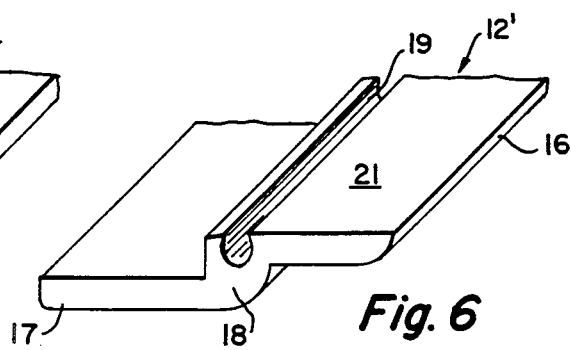
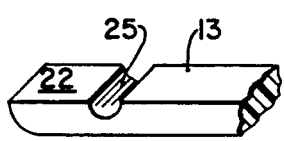
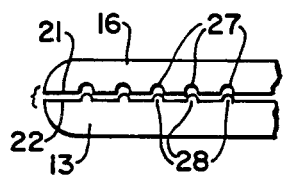
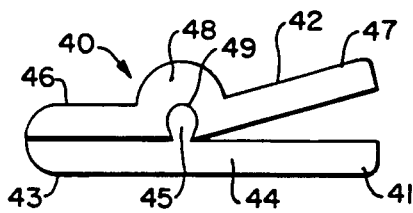
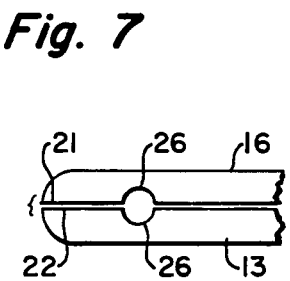
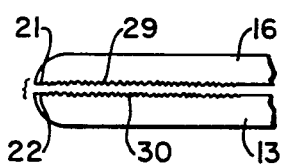
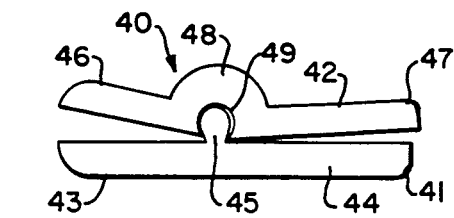

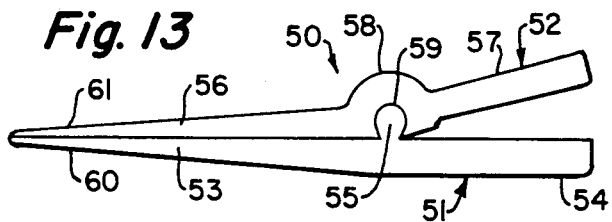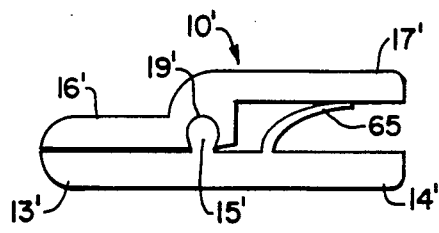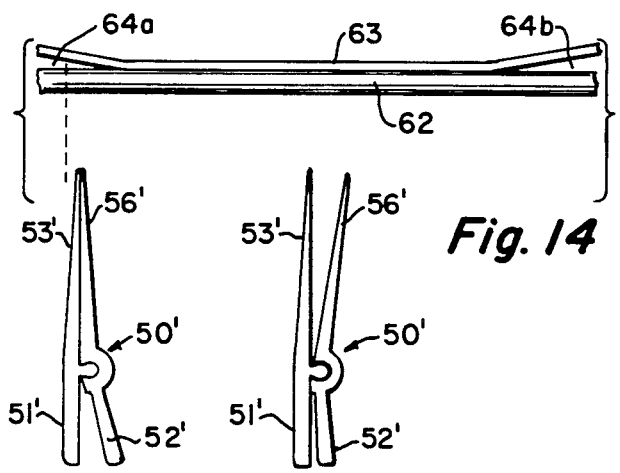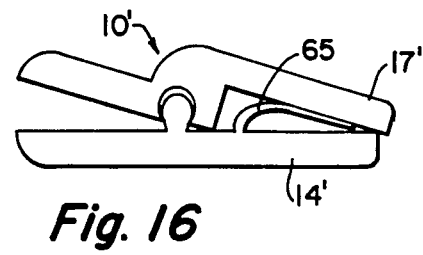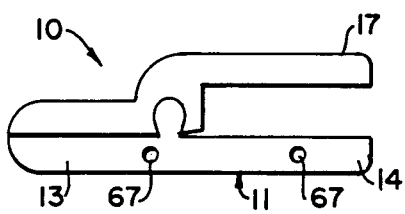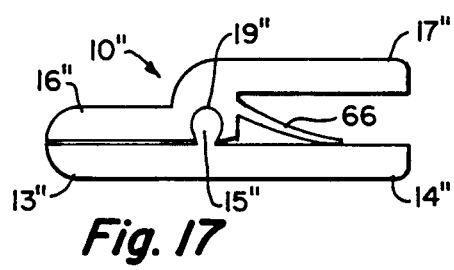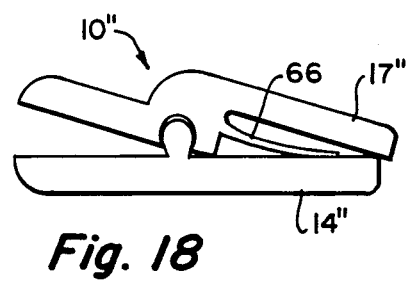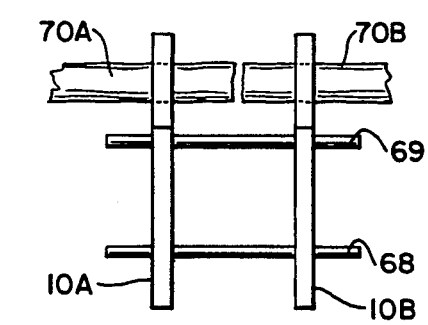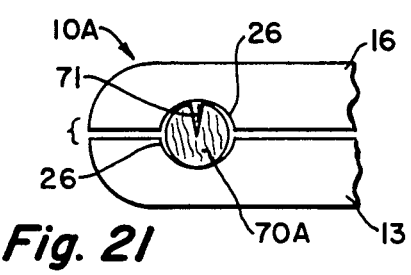

TENDON APPROXIMATOR

CROSS REFERENCES TO RELATED APPLICATIONS

This application is a division of our earlier filed U.S. patent application Ser. No. 263,518, filed Oct. 27, 1988, now U.S. Pat. No. 4,957,500.

BACKGROUND OF THE INVENTION

1. Field of the Invention

The present invention concerns a normally closed clamp and more particularly a normally closed disposable surgical clamp particularly adapted to pinch a blood vessel (artery or vein) and to prevent flow of blood through the blood vessel during surgical procedures. The clamp may be effectively used as a separator as its jaws open from the normally closed position. Two of the clamps may be joined in a useful tendon approximator for use in tendon ligating procedures.

2. Description of the Prior Art

There are numerous available normally closed clamps which are employed in surgical procedures. Many of the clamps are made of stainless steel or other sterilizable materials which, because of their expense, must be recovered, autoclaved or otherwise sterilized, and reused. Many of the surgical clamps generate excessive closing pressures in their normally closed position and as a result may cause damage to the delicate walls of pinched blood vessels. Some of the available surgical clamps require special tools for opening the jaws of the clamp to receive a blood vessel. Some clamps require a special tool to re-open and remove the clamps when the surgical procedure is completed.

There is a need for a lightweight, inexpensive, sterile clamp which can be employed as a surgical clamp, easily opened when desired, providing adequate but not excess closing jaw pressure, easily removed without the need of additional tools and sufficiently inexpensive to justify single use without requiring recovery and re-sterilization.

STATEMENT OF THE PRESENT INVENTION

According to the present invention, a two-piece clamp is provided. Preferably each part is extruded linearly or molded from lightweight, flexible, plastic substances. The linear extrusions are sliced transversely to produce a clamp base member and a clamp clamping member which are slide-fitted together to form a normally closed clamp having normally closed jaws at one end and normally spaced-apart handle members at the other end. In the central region of the normally closed clamp, a cam member is provided on the base member and a cam-engaging surface is provided on the clamping member. The cam member and the cam-engaging surface are engaged at least in part. The surface of the cam member is a non-circular, arcuate surface. The cam-engaging surface applies a torque urging the jaw members into proximity and provides a greater torque when the jaw members are spaced-apart as a result of drawing together the handle members.

The clamp can be used by an operating surgeon or his operatory assistants. The normally closed clamp is opened by squeezing the handle members together. The normally closed clamp returns to its normally closed position when the handle members separate. The two components are preferably fabricated from inexpensive, lightweight, plastic substances such as polyethylene, polypropylene, polyurethane, polyesters, polyamides, polycarbonates and other substances which are limitedly flexible. The clamp base member does not require the limited flexibility and may be fabricated from other materials such as rigid plastics, metals, e.g., extruded aluminum alloy.

The normally closed clamp can also be employed as a separator device or a spreading device. The jaw members of the normally closed device can be placed between two tissues and the handle members can be brought together whereby the jaw members spread apart to separate the tissues. In this use, the jaw members are preferably tapered and provided with blunt tips to avoid tissue damage. The advantage of the present normally closed spreading device as a tissue separator is that the operator can spread the jaw members conveniently by squeezing the handle members. Moreover the extent of movement of the jaw members is predictable; excessive spreading cannot occur which might result in damage to the separated tissues. This should be contrasted with the present tissue spreaders which function in the manner of scissors—the surgeon spreads apart the handle members causing a corresponding spreading of the spreader jaw members. Such spreading devices can be opened excessively causing tissue damage.

The normally closed device also may be employed as a membrane separator, particularly in delicate surgical procedures such as the Janneta procedure in which the surgeon separates a nerve from a blood vessel. The Janneta procedure employs a surgical cutting to separate a blood vessel from an engaged nerve. Because of the size of the blood vessels and nerves, the surgery is delicate and has many pitfalls. The present device permits gentle separation of a nerve from an adjoining blood vessel. The relative movement of the jaws is undirectional—that is, one jaw (the base element jaw) remains stationary while the other jaw moves laterally and can slide between the contacting nerve and blood vessel. In this manner the nerve is separated from the blood vessel without requiring surgery. For this separating use, the device should have tapering, blunt-tipped jaw members.

A still further use of the present clamp members is in tendon approximation. Tendon approximators are employed to retain abutting tendon ends in confrontation to permit surgical ligation of the tendon. The present clamp members may be provided with one or more bores extending transversely through one or both of the elements. A rigid wire or rod, preferably stainless steel, is press-fitted into the bore of each of two clamps. Each clamp retains one end of a tendon. The two clamps may be advanced toward each other by sliding along the one or more wires or rods until the tendon ends are in confrontation. The clamps will retain that configuration until the tendon ligation is completed.

A still further alternative to the present invention is to provide an extruded arcuate finger on one or the other of the clamp members such that the arcuate finger, extending from one handle member, is engaged with the inner surface of the other handle member. When the handle members are drawn together, the arcuate finger is further distorted and applies an increasing torque tending to return the clamp to their normally closed position. When the handle members are released, the arcuate finger applies a torque tending to restore the normally closed condition. The arcuate finger may be employed in addition to the non-circular cam surfaces previously described to maintain the normally closed configuration. Alternatively the cam surfaces may be circular and all of the restoring torque may be provide from the arcuate finger.

A further embodiment of the invention is adapted for use as a towel clamp. At the present time, surgical steel towel clamps are employed to connect toweling which drapes those regions of a surgical patient's anatomy which are not exposed during the particular surgical procedure. Multiple clamps are used to secure the disposable fabric. The existing towel clamps are normally surgical steel instruments which are recovered, autoclaved and reused. In this embodiment of the invention, the jaw members have concave confronting surfaces and terminate in a tip which preferably sharpened or pointed. In the normally closed position, the jaw members are urged into tip-to-tip engagement and the concave jaw surfaces provide an opening for receiving fabric edges. In this embodiment, the normally closed clamps can be discarded along with the towels.

In a still further embodiment, a normally closed clamp is provided with jaw liners formed from soft pliable material such as plastic, rubber or preferably foamed polymeric substances. The inserts may be secured to a confronting jaw surface by means of adhesives or other fastening techniques. By employing dual durometer extrusion procedures, the soft pliable jaw liner can be extruded directly into the clamp element.

DESCRIPTION OF THE DRAWINGS

FIG. 1 is a side elevation of the two piece, normally closed clamp in its normally closed position.

FIG. 2 is a side elevation of the normally closed clamp in its open position.

FIG. 3 is a perspective illustration of the clamp of FIGS. 1 and 2 having a vessel secured between the jaws.

FIG. 4 is a side elevation of the normally closed clamp showing a vessel pinched between the jaws.

FIGS. 5 and 6 are fragmentary illustrations of extrusion blanks for producing the normally closed clamp.

FIG. 7 is a fragmentary illustration of a base jaw member showing a transverse channel.

FIG. 8 is a side elevation of confronting jaw members with confronting channels.

FIG. 9 is a side elevation of confronting jaw members having corresponding grooves and beads.

FIG. 10 is a side elevation of confronting jaw members having serrations on the confronting jaw faces.

FIGS. 11 and 12 are side elevations of an alternative construction of the present normally closed clamp in the normally closed position (FIG. 11) and in the open position (FIG. 12).

FIG. 13 is a side elevation of a normally closed clamp having tapered, blunt-tipped jaw members for use as a tissue spreader.

FIG. 14 is a sketch showing the use of the normally closed spreader device for separating a vein from an engaging blood vessel.

FIG. 15 is a side elevation of an alternative embodiment of the normally closed clamp in the normally closed position.

FIG. 16 is a side elevation of the embodiment of FIG. 15 in the open position.

FIG. 17 is a side elevation of a further embodiment of the normally closed clamp in its normally closed position.

FIG. 18 is a side elevation of the embodiment of FIG. 17 in its open position.

FIG. 19 is a side elevation of the normally closed clamp illustrating bores in the base element.

FIG. 20 is a plan view of two normally closed clamps of the type shown in FIG. 19 connected together to function as a tendon approximator.

FIG. 21 is a fragmentary side elevation of modified jaw elements of FIG. 8 engaged in their normally closed position with a secured tendon.

DESCRIPTION OF THE PREFERRED EMBODIMENTS

Figure 22:
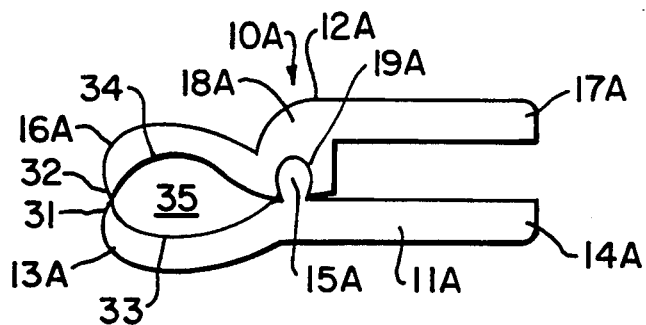
FIGS. 22 and 23 are side elevation views of a further alternative construction of the present normally closed clamp in the normally closed position (FIG. 22) and in an open position (FIG. 23).

FIG. 1 is a side elevation of the present, normally closed clamp 10 having a base member 11 and a clamping member 12. The base member 11 includes a jaw member 13, a handle member 14 and a central, non-circular, cam element 15. The clamping member 12 includes a jaw member 16, a handle member 17, a central body member 18 including a cam-engaging surface 19 which is engaged at least in part with the surface of the central, non-circular, cam element 15.

It will be observed in FIG. 1 that the normally closed clamp 10 has its jaw members 13, 16 in a normally closed relation and its handle members 14, 17 in a normally spaced-apart relation. The cam-engaging surface 19 corresponds to the surface of the cam element 15 and the plastic material forming the clamping member 12 has a minimum flexure urging the jaw members 13, 16 into proximity.

In FIG. 2, the handle members 14, 17 are drawn together and the jaw members 13, 16 are spaced-apart. Confronting surfaces 21, 22 are presented angularly to one another. It will be further observed from FIG. 2 that the cam-engaging surface 19 has been distorted from its normal shape and the surface 19a has advanced upwardly along the surface 20 of the cam element 15, causing a change in shape of the cam-engaging surface 19 which creates increased flexural stress tending to urge the cam-engaging surface 19 back into its normal position relative to the cam element 15. When the handle members 14, 17 are released, the flexural stress in the cam-engaging surface 19 causes the clamp 10 to return to its normally closed position and, as shown in FIG. 3 and FIG. 4, to pinch a vessel 23 which is positioned between the jaw members 13, 16.

As shown in FIG. 4, beads 24 may be provided in the outer surfaces of the handle members 14, 17 to facilitate gripping the clamp handle member 14, 17.

The base member 11 may be fabricated from non-flexible materials such as aluminum alloy, stainless steel or rigid plastics. The clamping member 12 is formed from a limitedly flexible plastic such as polyethylene, polypropylene, polyurethane, polyesters, polyamides, polycarbonates and other materials which have sufficient rigidity to retain their shape when the clamp is opened—that is, the jaw member 16 and handle member 17 move together, yet the cam-engaging surface 19 distorts over the outer surface 20 of the cam member 15 as the clamp is opened and closed.

Preferably the clamping member 12 and base member 11 are formed from linear extrusions of the selected thermoplastic material as shown in FIGS. 5 and 6. FIG. 5 illustrates the extrusion 11' for the base member 11. FIG. 6 illustrates the extrusion 12' for the clamping member 12. Each of the extrusions 11', 12' is sliced into transverse sections having a thickness of about 1 to 15 millimeters.

Additional features of the clamps may include a transverse channel 25 in the base jaw member 13 as shown in FIG. 7. The channel 25 will secure the location of a vessel between the clamp jaws.

As shown in FIG. 8, a channel 26 may be provided in each of the jaw members 13, 16 to secure the location of a retained vessel.

In order to provide improved gripping between the jaw members, a plurality of grooves 27 and a plurality of corresponding beads 28 may be extruded in the clamping jaw member 16 and the base jaw member 13 respectively as shown in FIG. 9.

FIG. 10 illustrates serrations which are extruded in the confronting surfaces 21, 22 of the clamping jaw member 16 and base jaw member 13 respectively to improve gripping action of the clamp.

An alternative embodiment of the present invention is illustrated in FIGS. 11, 12 wherein the clamp 40 is shown in a normally closed position in FIG. 11 and in an open position in FIG. 12. The clamp 40 has a base member 41 and a clamping member 42. The base member 41 includes a base jaw member 43, a base handle member 44 and a base cam member 45. The clamping member 42 has a clamping jaw member 46, a clamping handle member 47 and a central body member 48 which includes a cam surface 49. In the normally closed position of FIG. 11, the jaw members 43, 46 are in proximity and the handle members 44, 47 are spaced-apart. In this condition, the cam member 45 and cam surface 49 exert a minimum torque tending to urge the jaw members 43, 46 into proximity. When the handle members 44, 47 are brought together as shown in FIG. 12, the cam surface 49 slides over the cam member 45 and the jaw members 43, 46 are spread-apart. The torque applied by the cam members 45 and cam surface 49 in the clamp-open position of FIG. 12 is greater than the torque existing in the normally closed clamp position of FIG. 11. It will be observed that the cam member 45 has a non-circular, arcuate shape and that the cam surface 49 has a corresponding non-circular, arcuate shape. The flexure of the cam surface 49 causes the clamp 40 to seek the normally closed position shown in FIG. 11.

Use As A Separator

The normally closed clamp of this invention also may be employed as a separator for separating tissues. The jaw members of the clamp are tapered and provided with blunt tips as shown in FIG. 13. The separator device 50 (also a normally closed clamp) has a base element 51 and a pivotal element 52. The base element 51 has a tapered jaw member 53, a handle member 54 and a central cam member 55. The pivotal member 52 includes a tapered jaw member 56, a handle member 57 and a central body portion 58 including a cam engaging surface 59. Each of the tapered jaw members 53, 56 is provided with a blunt tip 60, 61 respectively.

The separator device 50 can be employed in surgical procedures where it is desirable to spread apart body tissues or tendons, blood vessels, nerves, et cetera. When the handle members 51, 57 of the separator device 50 are drawn together, the jaw members 53, 56 spread apart to a known width. This is particularly important. The state-of-the-art spreader devices employ a scissors principle which requires the operating surgeon to spread the scissors handle elements in order to spread the scissors jaw elements. Normally there is no stop mechanism on the existing separator devices. Excessive spreading may cause tissue damage.

A specialized use of the separator device of FIG. 13 is illustrated in FIG. 14. A surgical procedure known as the Janneta procedure is employed to separate a nerve which may be positioned in contact with a small blood vessel. Customarily in the Janneta procedure, a nerve is cut away from the engaging blood vessel by means of a sharp knife. Such cutting requires care and delicacy and presents opportunities for error. As illustrated in FIG. 14, a blood vessel 62 is shown in contact with a nerve 63. The nerve 63 and blood vessel 62 are separated at the spaces 64a, 64b. The tapered jaw members 53', 56' of the spreader device 50' are introduced (as indicated by the broken line) into the space 64a between the nerve 63 from the blood vessel 62. The operating surgeon squeezes the handle members 51', 52' until the clamping jaw 56' moves to the right while the base jaw 53' remains in the space 64a. Thus the tapered jaw member 56' slides between the nerve 63 and blood vessel 62 urging a separation. The separator device 50' is moved along the length of the blood vessel 62 until the engagement with the nerve 63 is entirely opened at the space 64b. Thereafter, in the Janneta procedure, a permanent spacer is positioned between the blood vessel 62 and the nerve 63 to prevent recurrence of the contact.

Alternative Construction

As shown in FIGS. 15-18, the resiliency needed to maintain the clamp in a normally closed position may be provided from an arcuate finger of resilient plastic material which functions as a spring element. In FIG. 15, 16, the clamp 10' has an arcuate finger 65 extending from the inner face of the base handle member 14' to the inner surface of the clamping handle 17'. In the normally closed condition of FIG. 15, the arcuate finger 65 is distorted and applies a torque urging the handle members 14', 17' open and consequently urging the jaw members 15', 13' into proximity. When the handle members 14', 17' are brought together as shown in FIG. 16, the arcuate finger member 65 is further distorted, thereby increasing the torque urging the clamp 10' toward its normally closed position.

Alternatively, as shown in FIGS. 17, 18, an arcuate finger member 66 may be an extension from the clamping handle member 17'''' which engages the inner surface of the base handle member 14'', and exerts a torque urging the jaw members 13'', 16'' into proximity. When the handle members 17'', 14'' are squeezed together as shown in FIG. 18, the arcuate finger member is further distorted and exerts a greater torque.

The arcuate finger elements 65, 66 preferably are extruded when the resilient plastic elements (FIG. 5, FIG. 6) are extruded and are an integral element of the extrusions 11', 12'.

The arcuate finger elements 65, 66 may be the sole resilient elements urging the normally closed clamp into its normally closed condition. Alternatively, the arcuate finger elements 65, 66 may provide a torque in addition to that which is achieved from the cam member 15' (15'') and the cam engaging surface 19' (19'').

Tendon Approximator

The present normally closed clamp, as shown in FIG. 19, may be provided with one or more bores 67 which extend transversely through the clamp, preferably, through the base member 11.

As shown in FIG. 20, two or more of the present normally closed clamps 10A, 10B are positioned parallel to each other and one or more rigid rods 68, 69 are press-fitted into the bores 67 of the clamps 10A, 10B to support the clamps 10A, 10B in a parallel relationship. The resulting assembly functions as a tendon approximator. As shown in FIG. 20, two ends of a tendon 70A, 70B are clamped in the clamps 10A, 10B, respectively. The clamps 10A, 10B are then drawn together by sliding one or both of the clamps 10A, 10B along the rods 68, 69. With the abutting ends of the tendon 70A, 70B in confrontation, an operating surgeon can carry out a tendon ligation procedure.

The clamps 10A, 10B may be made more effective for use in the tendon approximator assembly as shown in FIG. 21. The jaw elements 16, 13 of FIG. 8 are reproduced in FIG. 21 with a sharp spike element 71 extending from an arcuate groove 26 of one jaw element 16 into the arcuate groove 26 of the opposing jaw element 13. The sharp spike 71 penetrates the tendon 70A to improve the resistance to tendon pullout from the clamp 10A.

Towel Clamp

A further embodiment of the present normally closed clamp is particularly useful as a towel clamp. In many surgical procedures, the anatomy of a surgical patient which is not exposed during the surgical procedure is covered with drapes or towels, usually made from non-woven fabric and intended to be discarded after a single use. In order to secure the towels during the surgical procedure, the present practice is to use pointed clamps called towel clips which are customarily fabricated from surgical steel and which are recovered after each operation for sterilization and reuse. The clamps are initially expensive and they require costly sterilization between uses.

Figure 23:
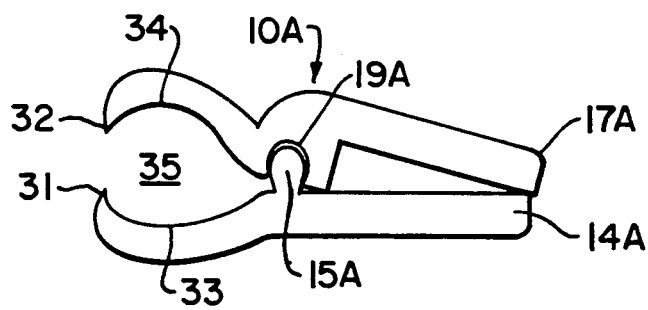

A normally closed clamp as illustrated in FIGS. 22, 23 permits single, throwaway use of an inexpensive normally closed clamp. As shown in FIGS. 22, 23, the towel clamp embodiment 10A includes a base member 11A and a clamping member 12A. The base member 11A includes a handle member 14A, a cam element 15A and a base jaw member 13A. The clamping member 12A includes a handle 17A, a clamping jaw member 16A, a central body member 18A and a cam engaging surface 19A. The base jaw member 13A has a forward tip 31 and a concave surface 33 which confronts the clamping jaw member 16A. The clamping jaw member 16A has a forward tip 32 and a concave surface 34 confronting the base jaw member 13A. The two concave surfaces 33, 34 define an opening 35 between the jaw members 13A, 16A.

At least one of the tips 31, 32 is preferably sharpened to a beveled or pointed edge in order to provide a firm engagement with a clamped fabric. In the open position of the clamp 10A shown in FIG. 23, the handle members 14A, 17A are brought together and the tips 31, 32 separate to provide a throat for receiving within the opening 35 a substance to be secured by the clamp, for example, the fabric forming surgical drapes.

Tubing Clamp

A further embodiment of the present normally closed clamp is particularly useful as a tubing clamp.

Figure 24:
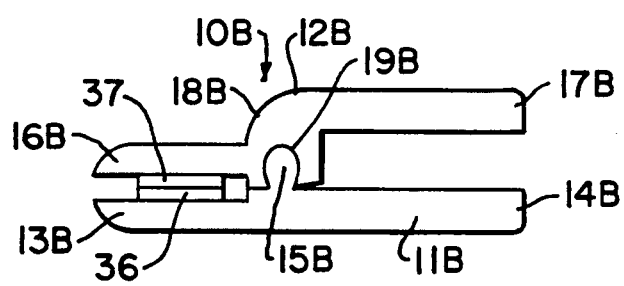
FIGS. 24 and 25 are side elevation view of a still further embodiment of the present normally closed clamp in the normally closed position (FIG. 24) and in an open position (FIG. 25).
Figure 25:
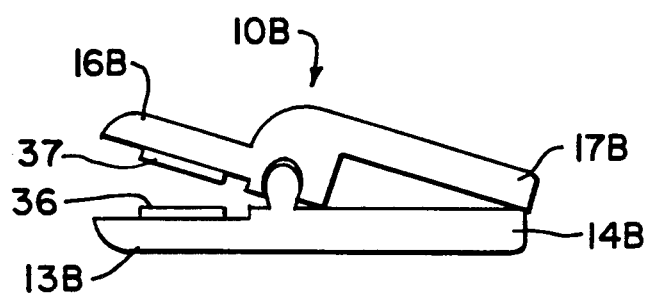

A normally closed clamp as illustrated in FIGS. 24, 25 provides soft resilient liners. The clamp 10B includes a base member 11B and a clamping member 12B. The base member 11B includes a handle member 14B, a cam element 15B and a base jaw member 13B. A clamping member 12B includes a handle 17B, a clamping jaw member 16B, a central body member 18B and a cam engaging surface 19B. The base jaw member 13B has a pad 36 which confronts the clamping jaw member 16B. The clamping jaw member 16B has a pad 37 confronting the base jaw member 13B. The two pads 36, 37 are formed from a soft, resilient substance, such as a pliable plastic, preferably a foamed polymeric composition such as a foamed polyurethane elastomer. The pads 36, 37 may be preformed and secured to the jaw members 13B, 16B by adhesives or other fastening means. The pads 36, 37 may be extruded integrally with the clamp members 11B, 12B respectively by well known dual durometer extrusive procedures.

The lined clamp of FIGS. 24, 25 is of particular value as a tubing clamp to close fragile tubing without damage to the tubing walls.

FIG. 25 shows the clamp 10B in its open condition with the two pads 36, 37 spaced-apart to receive an element (not shown) which is to be clamped.

We claim:

1. A tendon approximator including two normally closed clamps, each clamp comprising two connected elements including:

a base element having a base jaw member, a base handle member and a central, non-circular arcuate cam member; a clamping element having a clamping jaw member, a clamping handle member and a non-circular arcuate cam-engaging member; said base element being secured to said clamping element by engagement of at least a portion of said cam-engaging member with said cam member; said base jaw member and said clamping jaw member having confronting surfaces which are in proximity when said cam-engaging member conforms to the surface of said cam member;

each said clamp having two transverse bores; a pair of rods fitting in corresponding ones of said bores to support the said two clamps in generally parallel relation; at least one of said clamps being slideable along the said rods with respect to the other of said clamps.

2. A tendon approximator as defined in claim 1 wherein the said jaw members of one clamp have corresponding transverse channels to receive a tendon.

3. The tendon approximator of claim 2 wherein a sharp spike is positioned in one of the said channels to penetrate and retain a tendon within the said one of said channels.

* * * * *